(12) United States Patent
Miyamoto et al.

(10) Patent No.: US 7,691,413 B2
(45) Date of Patent: Apr. 6, 2010

(54) COMPOSITE PARTICLE AND PROCESS FOR PRODUCING THE SAME

(75) Inventors: Masafumi Miyamoto, Wakayama (JP);
Yasushi Sasaki, Wakayama (JP);
Toshiya Shimada, Wakayama (JP);
Shinobu Hiramatsu, Wakayama (JP)

(73) Assignee: Kao Corporation, Tokyo (JP)

( * ) Notice: Subject to any disclaimer, the term of this patent is extended or adjusted under 35 U.S.C. 154(b) by 743 days.

(21) Appl. No.: 11/231,991

(22) Filed: Sep. 22, 2005

(65) Prior Publication Data

US 2006/0067895 A1    Mar. 30, 2006

(30) Foreign Application Priority Data

Sep. 29, 2004   (JP)   ............... 2004-283418
Dec. 24, 2004   (JP)   ............... 2004-372886

(51) Int. Cl.
*A61K 33/30*   (2006.01)
*A61K 9/14*   (2006.01)
*A61K 8/27*   (2006.01)

(52) U.S. Cl. ............ 424/497; 424/489; 424/498; 424/641; 424/642; 424/59

(58) Field of Classification Search ............... 424/401, 424/489, 641, 497, 498, 642, 59
See application file for complete search history.

(56) References Cited

U.S. PATENT DOCUMENTS 6,060,084 A    5/2000   Sullivan et al.
6,368,586 B1   4/2002   Jacob et al.
2004/0001869 A1 *  1/2004   Yago et al. ............... 424/401

FOREIGN PATENT DOCUMENTS

| EP | 1 243 325 A1 | 9/2002 |
| JP | 3-183620 | 8/1991 |
| JP | 6-167835 | 6/1994 |
| JP | 8-53568 | 2/1996 |
| JP | 11092599 | * 4/1999 |
| JP | 11-302015 | 11/1999 |

* cited by examiner

*Primary Examiner*—John Pak
(74) *Attorney, Agent, or Firm*—Oblon, Spivak, McClelland, Maier & Neustadt, L.L.P.

(57) ABSTRACT

The invention provides a composite particle, a process for producing the same, and cosmetics containing the same The invention relates to composite particles containing a polyolefin-based resin having a crystallization degree of 80% or less and zinc oxide and obtained by hot melt microencapsulation or spray cooling, or composite particles containing a polyolefin-based resin having a crystallization degree of 80% or less and zinc oxide, wherein the degree of remaining zinc oxide in the particles is 50 wt % or more after being dipped for 1 hour in 0.5 mol/L hydrochloric acid solution at 25° C. (solution composition: water and ethanol in equal volumes), a process for producing the composite particles, and cosmetics containing the composite particles.

18 Claims, 1 Drawing Sheet

COMPOSITE PARTICLE AND PROCESS FOR PRODUCING THE SAME

FIELD OF THE INVENTION

The present invention relates to composite particles containing polyolefin-based resin and zinc oxide, a process for producing the same, and cosmetics containing the same.

BACKGROUND OF THE INVENTION

In recent years, an increase in the level of UV rays reaching the surface of the earth, caused by partial depletion of the ozone layer, is regarded problematic, and there is demand for sun-screening cosmetics having a higher effect than conventional. Conventionally, organic compounds, for example those based on benzophenone, benzoic acid or methoxycinnamic acid, are used as UV absorbers in such sun-screening cosmetics, but these organic compounds cannot absorb UV rays in a broader wavelength range and irritate the skin. Because of these problems, there is a need for safer UV-screening agents.

It has been revealed that UV rays reaching the surface of the earth cause skin aging and cancers by the synergistic effect of UV rays of short wavelengths (UV-B region: 280 to 320 nm) causing inflammations (so-called sunburns) such as blisters and red spots, with UV rays of longer wavelengths (UV-A region: 320 to 400 nm), and in recent years, there is significant interest in screening of UV rays particularly in the UV-A region.

Zinc oxide originally shows a sharp edge of absorption in the vicinity of 380 nm, and thus has a higher screening effect against UV rays in the UV-A region, and later, superfine particles of zinc oxide have been developed. The superfine particles of zinc oxide shield from UV rays in a broad wavelength range from the UV-B region to the UV-A region, and the superfine particles of zinc oxide are excellent in transparency with a lower refractive index of 2.0 than the refractive index (2.7) of superfine particles of rutile titanium oxide, and thus attract attention as a UV-shielding agent.

On one hand, zinc oxide is inherently soluble in a very small amount in water, and by virtue of the physiological action of its eluted zinc ion, it has been utilized for a long time as an astringent in the field of cosmetics. Further, zinc oxide has such chemical reactivity as to react with fatty acid to form metallic soap, thus absorbing sebum secreted from the skin to improve retention of cosmetics on the skin and absorbing body-odor components to exhibit a deodorant effect.

However, such physiological activity and chemical reactivity tend to be further increased by converting zinc oxide into superfine particles, and when higher safety for skin tissues is to be required in the future, the activity of the particle surface is desirably suppressed.

The water solubility and chemical reactivity of zinc oxide described above bring about various inconveniences in designing the formulation of cosmetics. That is, the most important starting component in cosmetics is water also serving as a major constituent component in the human body, and in the cosmetics containing superfine particle of zinc oxide, its zinc ion eluted into water reacts with another component, and thus the ratio of water cannot be increased, thus limiting the freedom of formulation. In the case of sun-screening cosmetics containing conventional superfine particles of zinc oxide, for example, it is difficult to increase the ratio of water to 50% or more, and the majority of emulsified products are limited to those of water-in-oil type (W/O). These emulsified products are based on oil, thus hardly achieving dry feeling.

Use of the superfine particles of zinc oxide in cosmetics also limits the freedom of formation because the superfine particles react with other various ingredients such as an oil, perfume, coloring matter, organic UV absorber and water-soluble polymer in the cosmetics, to cause problems such as an increase or decrease in the viscosity of the cosmetics, generation of a nasty smell, discoloration etc.

Under these circumstances, JP-A 3-183620 discloses an art wherein the surfaces of fine particles of zinc oxide are coated with an oxide or hydroxide of aluminum, silicon, zirconium or tin thereby reducing the catalytic activity of zinc oxide to suppress the denaturation of organic vehicles in cosmetics and further reducing the dynamic coefficient of friction of zinc oxide to prevent deterioration in smoothness and feeling.

JP-A 11-302015 discloses an art which contains arranging a high-density coating layer consisting of silicon oxide on the surface of a zinc oxide particle to suppress the solubility thereof in purified water.

JP-A 8-53568 discloses an art which includes converting a monomer phase having zinc oxide dispersed therein into particles by suspension polymerization or emulsion polymerization to suppress the action of zinc oxide on other components such as vehicles. Generally, the monomer used in the suspension or emulsion system includes styrene, methyl methacrylate, acrylonitrile, vinyl acetate etc., but any of the resulting polymers are poor in chemical resistance.

Methyl methacrylate used in the Examples in JP-A 8-53568 supra has an ester linkage, and thus it cannot be said that the resulting polymer is satisfactory in respect of chemical resistance. Further, the resulting particles are generally swollen with ethanol or oil incorporated into cosmetics, thus failing to arrive at substantially sufficient inhibition of the reaction of zinc oxide with other components such as vehicles.

On one hand, fine particles themselves generally easily form an aggregate. Accordingly, fine particles are dispersed in a monomer and fixed by polymerizing the monomer, or fine particles are kneaded with, and dispersed in, a molten resin and then fixed by solidifying the resin.

In the method of fixing fine particles in resin by solidifying the resin, the resin is sprayed in a molten state into a gaseous phase in order to reduce the particle diameter of the resin, or the resin is solidified and then milled.

Accordingly, JP-A 6-167835 discloses a technique of spray-cooling a molten resin via a rotating disc type nozzle.

SUMMARY OF THE INVENTION

The invention provides composite particles containing a polyolefin-based resin having a crystallization degree of 80% or less and zinc oxide and obtained by hot melt microencapsulation or spray cooling.

The invention provides composite particles containing a polyolefin-based resin having a crystallization degree of 80% or less and zinc oxide, having a degree of remaining zinc oxide in the particles of 50 wt % or more after having been dipped for 1 hour in 0.5 mol/L hydrochloric acid solution at 25° C. (solution composition: water and ethanol in equal volumes)

The invention provides cosmetics containing the composite particles.

The present invention also provides a process for producing the composite particles, including mixing polyolefin-based resin with zinc oxide and then cooling and solidifying the mixture by spraying it into a refrigerant at a temperature not lower than the melting point or softening point of the polyolefin-based resin.

BRIEF DESCRIPTION OF THE DRAWINGS

The reference numerals in the drawings are follows:
1: Flow path of a melt admixture of resin and zinc oxide
2: Flow path of spray gas
3: Spray particles
4: Nozzle edge
5: Collision focal spot

DETAILED DESCRIPTION OF THE INVENTION

The fine particles of zinc oxide provided thereon with a coating layer in JP-A 3-183620 supra are still poor in suppression of optical catalyst activity, and particularly water solubility and chemical reactivity inherent in zinc oxide are hardly suppressed.

As shown in the Examples in JP-A 11-302015 supra, a slight reduction in viscosity is recognized in a product stored at room temperature for 7 days.

The particle diameter of resin particles obtained by the method in JP-A 6-167835 supra is about 30 to 200 μm, so there is a limit to the reduction of the particle diameter.

To solve the above-described various problems of zinc oxide, particularly the problems of superfine particles of zinc oxide for use in sun-screening cosmetics, the present invention provides composite particles highly suppressing the surface activity of zinc oxide and having both high transparency and UV-screening properties, a process for producing the composite particles, and cosmetics containing the composite particles.

The composite particles of the present invention show significant suppression of the solubility of zinc oxide in purified water or in an aqueous solution of hydrochloric acid and exhibits suppression at high degree of the surface activity of zinc oxide, along with high transparency and UV-screening properties, and can be used preferably in cosmetics for UV screening.

In the process of the present invention, spraying can be conducted particularly via a 3-fluid or more nozzle to give composite particles wherein superfine particles of zinc oxide are uniformly dispersed in resin, the volume-average particle diameter of the composite particles is 30 μm or less, and the proportion of particles having a particle diameter of 5 μm or less is 15 vol-% or more.

[Polyolefin-Based Resin]

From the viewpoint of suppressing the surface activity of zinc oxide and reducing the solubility of zinc oxide, the polyolefin-based resin used in the present invention are polyolefin-based resin having a crystallization degree of 80% or less, more preferably 70% or less. In this case, different types of polyolefin-based resins may be used as a mixture insofar as the degree of crystallization of the polyolefin-based resin mixture is 80% or less.

The degree of crystallization can be determined by X-ray diffraction under the following measurement conditions.

<Conditions for Measurement by X-Ray Diffraction>
Unit: RINT 2500 manufactured by Rigaku Denki Co., Ltd.

Multiple peak separation method
Source of radiation: CuKα
Tube electric current: 120 mA
Tube electric voltage: 40 kV
Scan speed: 10°/min.

The polyolefin-based resin includes olefin homopolymers such as polyethylene, polypropylene, poly-1-butene, polymethyl pentene, polymethyl butene, polybutadiene etc., and olefin copolymers such as a propylene/ethylene random copolymer etc. Polyolefins having fluorine atoms such as in polytetrafluoroethylene (PTFE) etc. can also be used. Among these polyolefin-based resins, polyethylene is particularly preferable. From the viewpoint of improving the dispersibility of zinc oxide, acid-modified polyethylene is effective.

Preferably, the polyolefin-based resin used in the present invention has lower melt viscosity. The melting point or softening point of the polyolefin-based resin is preferably 80° C. or more, more preferably 100° C. or more, from the viewpoint of easy production of the composite particles. The upper limit is not particularly limited, but for easier production, the melting point or softening point is preferably 200° C. or less. The melting point of the polyolefin-based resin can be measured according to JIS K0064:1992.

From the viewpoint of the melt viscosity and strength of the resin, the molecular weight of the polyolefin-based resin is preferably 500 to 20000, more preferably 1000 to 10000. The molecular weight of the polyolefin-based resin can be determined by a viscosity method.

[Zinc Oxide]

Zinc oxide in the present invention is preferably zinc oxide having a particle diameter of 0.1 μm or less in order to attain UV-screening properties. Zinc oxide whose surface has been previously hydrophobated can be preferably used to improve its kneading with the polyolefin-based resin. The method of treating the surface of zinc oxide includes, but is not limited to, surface treatment with organopolysiloxane.

[Composite Particles]

The composite particles of the present invention are based on zinc oxide and polyolefin-based resin having a crystallization degree of 80% or less, and may contain other components, for example inorganic and organic pigments, a coloring matter such as an organic dye etc., a surfactant, a silicone compound, an antioxidant etc. unless the effect of the present invention is hindered.

From the viewpoint of applicability to a process described later and UV-screening properties, the polyolefin-based resin/zinc oxide ratio by weight in the composite particles is preferably 99/1 to 30/70, more preferably 95/5 to 50/50, still more preferably 80/20 to 60/40.

From the viewpoint of suppression of gritty feeling and frictional feeling, the volume-average particle diameter of the composite particles of the present invention is preferably 0.5 to 30 μm, more preferably 2 to 10 μm.

The volume-average particle diameter is a value determined in ethanol by using Coulter Counter (trade name: LS-230, manufactured by Beckman Coulter, Inc.).

[Process for Producing the Composite Particles]

The process for producing the composite particles of the present invention is preferably a hot melt microencapsulation method or a spray cooling method among which the spray cooling method is preferable. Other processes include a spray drying method, hybridization etc., but theoretically, these methods easily generate cracks and pores, thus making it difficult to shield zinc oxide from the outside world.

The hot melt microencapsulation method is a method wherein a dispersoid such as polyolefin-based resin, and zinc oxide, are dispersed in an environment at a temperature not lower than the melting point (or softening point) of the dispersoid in a dispersing medium not compatible therewith until a desired particle diameter is attained by utilizing mechanical shear force and the action of a surfactant, followed by cooling thereof to a temperature below the melting point (or softening point) of the dispersoid, to give solid particles. For example, the dispersoid includes polyethylene, and the dispersing medium includes water or glycerin. These procedures may be conducted under high pressure.

The spray cooling method is a method wherein polyolefin-based resin and zinc oxide are mixed with each other, and then the mixture at a temperature not lower than the softening point (or melting point) of the polyolefin-based resin is cooled and solidified by spraying it into a refrigerant. Composite particles obtained by this method hardly generate cracks and pores on the surfaces of the particles, and can shield zinc oxide from the outside world.

In the process of the present invention, polyolefin-based resin and zinc oxide are first preliminarily mixed with each other. From the viewpoint of achieving an excellent UV-screening effect, the compounding ratio of the polyolefin-based resin/zinc oxide by weight is preferably 99/1 to 30/70, more preferably 95/5 to 50/50, still more preferably 80/20 to 60/40. To achieve excellent UV-screening properties and transparency, their kneading is conducted desirably such that zinc oxide is dispersed in the state of nearly primary particles in the polyolefin-based resin. The apparatus used in kneading includes a plastomill, a planetary mixer, a roll mill, a kneader, an extruder etc.

Then, the resulting mixture is heated to a temperature not lower than the softening point (or melting point) of the polyolefin-based resin to give a thermally melt admixture which is then cooled and solidified by spraying into a refrigerant preferably at 5 to 50° C. through a multiple-fluid nozzle, for example a 1-fluid or more, preferably 2-fluid or more, more preferably 3-fluid or more nozzle, in a rotating disk atomizer, to recover the composite particles. Preferably, the admixture is sprayed together with a compressed gas into a refrigerant. The refrigerant is particularly preferably in a gaseous phase. The compressed gas used as fluid is a compressed gas or compressed nitrogen preferably at $9.8 \times 10^4$ Pa or more, more preferably at $9.8 \times 10^4$ to $29.4 \times 10^4$ Pa. This gas is preferably heated at a temperature not lower than the spray temperature in order to prevent the nozzle from clogging upon cooling thereby enabling continuous production of the particles.

Figure 1:
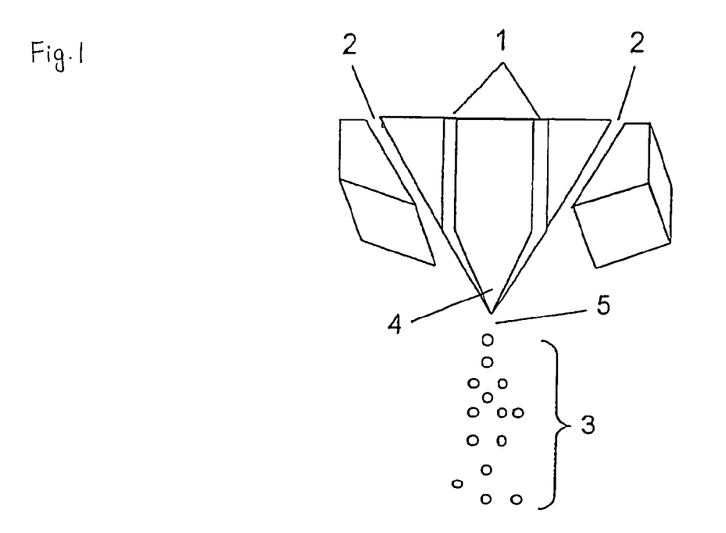
FIG. 1 is a view showing one example of a 4-fluid straight type nozzle.
Figure 2:
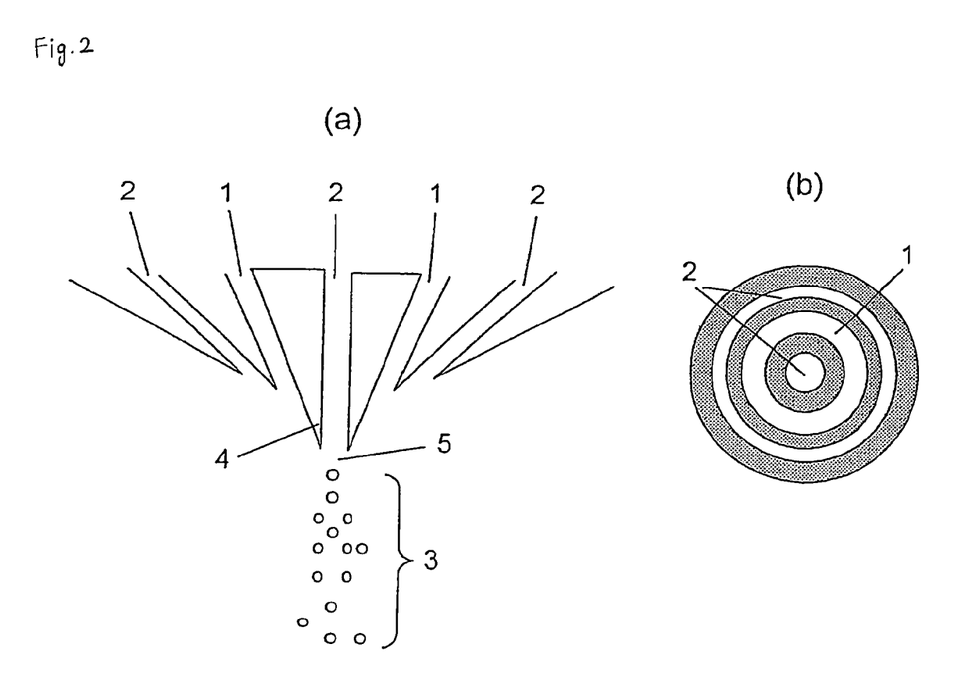
FIG. 2 is a view showing one example of a 3-fluid pencil type nozzle, wherein (a) is a front view, and (b) is a plan view.

From the viewpoint of simple structure and performance of converting the sprayed particles into fine particles, the multiple-fluid (3-fluid or more) nozzle is preferably a pencil type nozzle or a straight type nozzle, and particularly a 3-fluid pencil type nozzle and a 4-fluid straight type nozzle can be preferably used. The pencil type nozzle is more preferable than the straight type nozzle because the fluid speed at a collision focal spot, and fracture force, are higher due to the condensed stream. One example of the 4-fluid straight type nozzle is shown in FIG. 1, and one example of the 3-fluid pencil type nozzle is shown in FIG. 2. In FIG. 2, (a) is a front view, and (b) is a plan view. In FIGS. 1 and 2, 1 is a flow path of a melt admixture of resin and zinc oxide, 2 is a flow path of spray gas, 3 is a spray particle, 4 is a nozzle edge, and 5 is a collision focal spot.

As the 3-fluid pencil type nozzle and the 4-fluid straight type nozzle, a 3-fluid pencil type nozzle and 4-fluid straight type nozzle in Micro Mist Dryer MDL-050C manufactured by Fujisaki Electric Co., Ltd. can be preferably used.

In spraying the melt admixture through a nozzle, the spray gas/admixture ratio by volume is preferably at least 1000/1, more preferably at least 5000/1, from the viewpoint of obtaining fine particles. The upper limit of this volume ratio is not particularly present, but is preferably not higher than 100000/1 from an economical viewpoint.

From the viewpoint of achieving excellent spraying, the spray temperature is a temperature at which the viscosity of the mixture of polyolefin-based resin and zinc oxide becomes preferably 800 mPa·s or less, more preferably 300 mPa·s or less, further more preferably 100 mPa·s or less. The lower lit is not particularly present, but is preferably a temperature at which the viscosity becomes 10 mPa·s or more.

In the present invention, the composite particles may be treated with an anionic surfactant. The details are as follows.

[Treatment with an Anionic Surfactant]

In the present invention, the particles before treatment described above are treated with an anionic surfactant. Zinc oxide particles exposed to the surfaces of composite particles, or zinc oxide particles which in the vicinity of the surfaces of composite particles, occur in an easily eluting environment, can be coated with the anionic surfactant to give high stability to cosmetics blended with the composite particles.

The anionic surfactant used in the present invention is preferably the one forming a water-insoluble complex with a zinc ion. A method of easily confirming formation of the water-insoluble complex includes the following method.

The anionic surfactant is prepared as an about 0.1 to 1 wt % aqueous solution through which light transmittance can be visually recognized. Few drops of about 1% aqueous zinc chloride solution are mixed with 30 mL of the aqueous solution. When the aqueous solution of the anionic surfactant becomes turbid etc. upon mixing to reduce its transparency, formation of a water-insoluble complex consisting of a zinc ion and the anionic surfactant is meant.

Specific examples of the anionic surfactant showing this physical property include fatty acid salts, alkyl benzene sulfonates, alkyl sulfonates, dialkyl sulfosuccinates, N-methyl-N-alkyl taurine, alkyl phosphates, polyoxyethylene alkyl ether phosphates, fluoroalkyl benzoether carboxylates and fluoroalkyl benzoether phosphonates, and one or more of these can be used. The cation forming a salt with the anionic surfactant includes alkali metal ions, alkaline earth metal ions, ammonium ions, alkanol ammonium ions etc. Among these cations, alkali metal ions are preferable, and sodium ions and potassium ions are more preferable.

Among these anionic surfactants, alkyl phosphates whose alkyl residue contains 10 to 20 carbon atoms and N-methyl-N-alkyl taurine whose alkyl residue contains 10 to 20 carbon atoms are preferable.

Treatment of the particles before treatment with the anionic surfactant can be carried out by bringing the particles before treatment into contact with the anionic surfactant by a suitable method. Specifically, the particles before treatment are dispersed in a solution of the anionic surfactant and if necessary the composite particles are separated from the anionic surfactant solution. The anionic surfactant solution is preferably an aqueous solution, but there is the case where an alcohol such as ethanol can be mixed in a suitable amount to increase the affinity of the surface of a particle for the treatment solution thereby effecting the treatment more effectively. The mixing ratio of water/organic solvent by weight is preferably 100/0 to 20/80.

The amount of the anionic surfactant used in treatment is suitably 0.1- to 2-molar excess to zinc oxide in the particles before treatment. The concentration of the anionic surfactant in the treatment solution can be suitably regulated, and is preferably 0.01 to 6% by weight, more preferably 0.1 to 2% by weight. From the viewpoint of more selective insolubilization of zinc oxide in a part near to the surface of the particle, the treatment time is desirably a short time, preferably 1 minute to 10 hours, more preferably 3 minutes to 5 hours. For bringing the anionic surfactant into contact with the surface of the particle, a dispersing machine such as a homomixer or a high-speed impeller dispersing machine can be used effectively to cancel aggregation of the particles. The treatment temperature is not particularly limited insofar as it is lower than the temperature at which the particles are melted or aggregated.

The proportion of zinc oxide in the composite particles is not significantly changed by treatment with the anionic surfactant, and the proportion of zinc oxide can be measured from ignition residues of the composite particles before and after treatment. If necessary, other techniques such as ICP fluorescence analysis of a filtrate can also be used.

The content of zinc oxide in the composite particles after treatment is preferably 1 to 70% by weight, more preferably 5 to 50% by weight, still more preferably 10 to 40% by weight.

In the present invention, the composite particles may be treated with an acid and/or an alkali. The details are as follows.

[Treatment with an Acid and/or an Alkali]

In the present invention, the particles before treatment described above are treated with at least one member selected from an acid and an alkali. Zinc oxide particles exposed to the surfaces of composite particles, or zinc oxide particles which in the vicinity of the surfaces of composite particles, occur in an easily eluting environment, can be previously removed to give high stability to cosmetics compounded with the composite particles.

As the acid used in the present invention, an inorganic acid and an organic acid are used. The inorganic acid includes sulfuric acid, hydrochloric acid, nitric acid, phosphoric acid etc. The organic acid includes monovalent organic acids such as acetic acid, glycolic acid, propionic acid, lactic acid, gluconic acid etc., divalent organic acids such as fumaric acid, succinic acid, malic acid, tartaric acid etc., and trivalent organic acids such as citric acid, trimellitic acid (1,2,4-benzene tricarbonic acid) etc. As the molecular weight of the organic acid is increased, the organic acid tends to have higher permeability, thus dissolving zinc oxide in the inside of the composite particles. Accordingly, an organic acid having a molecular weight of 100 or more, particularly a molecular weight of 100 to 1000, is used more preferably.

The alkali used in the present invention includes sodium hydroxide, potassium hydroxide, ammonia, sodium bicarbonate, sodium carbonate etc.

Among the acid and alkali, the acid is preferable, and an inorganic acid or an organic acid having a molecular weight of 100 or more is more preferable.

Treatment with an acid and/or an alkali can be carried out by bringing the particles before treatment into contact with an acid and/or an alkali by a suitable method, and can be effected specifically by dispersing the particles before treatment in an acid and/or alkali solution and then separating the composite particles from the acid and/or alkali solution. The acid and/or alkali solution may be an aqueous solution, but a solution mixed with a water-soluble organic solvent such as ethanol can be used to increase the affinity of the surface of the composite particle for the treatment solution to effect the treatment more effectively. The mixing ratio of water/organic solvent by weight is preferably 100/0 to 20/80.

The amount of the acid and/or alkali used in treatment is suitably 0.1- to 2-molar excess to zinc oxide in the particles before treatment. The concentration of the acid and/or alkali in the treatment solution can be suitably regulated, and is preferably 0.01 to 6 mol/L, more preferably 0.1 to 2 mol/L. From the viewpoint of more selective solubilization of zinc oxide in a part near to the surface of the particle, the treatment time is desirably a short time, preferably 1 minute to 10 hours, more preferably 10 minutes to 5 hours. The treatment temperature is not particularly limited insofar as it is lower than a temperature at which the particles are melted or aggregated, and the temperature can be suitably determined from the treatment time and the amount of zinc oxide to be removed.

With respect to the amount of oxide zinc to be removed by the treatment, the treatment conditions are preferably those under which 1 to 50% by weight of zinc oxide contained in the particles before treatment is removed. The degree of removal of zinc oxide can be measured from ignition residues of the composite particles before and after treatment, and if necessary, other techniques such as ICP fluorescence analysis of a filtrate can also be used.

The content of zinc oxide in the composite particles after treatment is preferably 1 to 70% by weight, more preferably 5 to 50% by weight, still more preferably 10 to 40% by weight.

[Degree of Remaining Zinc Oxide in the Particles]

The composite particles of the present invention highly suppress the activity of zinc oxide, and as a standard in this evaluation, the degree of remaining zinc oxide in the particles after treatment with hydrochloric acid can be used. That is, zinc oxide will be inherently dissolved completely in acidic water, and thus the degree of remaining zinc oxide in the particles is determined by washing the composite particles with acidic water, then measuring the amount of zinc oxide, and comparing the amount of zinc oxide before and after washing with acidic water, to calculate the degree of remaining zinc oxide, on the basis of which the suppression of the surface activity can be evaluated. The degree of remaining zinc oxide in the composite particles of the invention after treatment with hydrochloric acid can be measured specifically according to a method shown in Test Example 1 shown later. When the degree of remaining zinc oxide in the particles after treatment with hydrochloric acid becomes nearer to 100 wt %, it is meant that the activity of zinc oxide becomes more suppressed.

The degree of remaining zinc oxide in the composite particles of the invention after treatment with hydrochloric acid is preferably 50 wt % or more, more preferably 70 wt % or more, still more preferably 80 wt % or more, further more preferably 90 wt % or more, and such composite particles can be stably used in emulsified products of oil-in-water type (O/W).

To determine the degree of remaining zinc oxide after treatment with hydrochloric acid, the content of zinc oxide can be measured from ignition residues of the composite particles, and if necessary, other techniques such as ICP fluorescence analysis of a filtrate can also be used.

[UV-Screening Properties and Transparency]

The composite particles of the present invention are preferably those satisfying both excellent UV-screening properties and transparency. As a standard in this evaluation, it is effective to use $\Delta T$ that is a difference between transmittance at a wavelength of 550 nm in the visible light range and transmittance at a wavelength of 350 nm in the UV light range, wherein the difference $\Delta T$ is determined by placing a uniform dispersion of the composite particles in silicone oil in a quartz cell having a light path of 50 μm in length, and then taking a transmission spectrum thereof by a spectrophotometer. Composite particles showing larger ΔT are those satisfying both excellent UV-screening properties and transparency at higher degrees.

The composite particles are mixed with silicone oil such that the amount of the composite particles, in terms of the amount of zinc oxide, becomes 1 part by weight relative to 100 parts by weight of silicone oil. As the silicone oil, SI-UGE (alkyl glyceryl ether-modified silicone, manufactured by Kao Corporation) can be preferably used. The difference ΔT is preferably 30% or more, more preferably 40% or more, still more preferably 50% or more.

[Cosmetics]

In the cosmetics of the present invention, the content of the composite particles of the present invention can be suitably selected depending on the object of the cosmetics, and is not particularly limited, but the content is preferably 0.1 to 50% by weight, particularly preferably 1 to 30% by weight.

The cosmetics of the present invention are not particularly limited with respect to form, and may be water-in-oil or oil-in-water emulsified cosmetics, oil cosmetics, spray cosmetics, stick-type cosmetics, aqueous cosmetics, sheet-type cosmetics and gel-type cosmetics. The type of the cosmetics of the present invention is not particularly limited either, and the cosmetics of the present invention include skin cosmetics such as a pack, foundation, lipstick, rouge, eye shadow, mascara, eye liner, eye blow, nail enamel, lotion, cold cream, hand cream, skin detergent, softening cosmetics, nutrient cosmetics, astringent cosmetics, whitening cosmetics, wrinkle-improving cosmetics, anti-aging cosmetics, cleansing cosmetics, antiperspirant and deodorant; and hair cosmetics such as a shampoo, rinse, treatment, hair-dressing and hair tonic, and the cosmetics are preferably cosmetics capable of exhibiting UV-screening properties and skin-hiding effect, more preferably those used as makeup cosmetics, sunscreen cosmetics and base cosmetics.

The cosmetics of the present invention can contain an alcohol. The alcohol includes C1-6 monohydric or polyhydric alcohols such as ethanol, glycerin, 1,3-butylene glycol, propylene glycol and sorbitol. In particular, a monohydric alcohol, particularly ethanol is preferable. The amount of the alcohol incorporated is preferably 5 to 30% by weight in the cosmetics of the present invention, particularly preferably 1 to 50 parts times by weight of the composite particles of the present invention.

Depending on the form, type etc. of the cosmetics, other conventional components can be further incorporated as cosmetic components into the cosmetics of the present invention in such a range that the effect of this invention is not hindered.

Such cosmetic components include, for example, extender pigments such as mica, talc, sericite, kaolin, nylon powder, polymethylsilyl sesquioxane and barium sulfate; solid pigments such as titanium oxide, zinc white and iron oxide; powders whose surface was rendered hydrophobic by treating these powders with silicone, metal soap or N-acyl glutamic acid; hydrocarbons such as solid or liquid paraffin, microcrystalline wax, vaseline, ceresin, ozokerite and montan wax; vegetable or animal fats and oils or wax, such as olive, ozokerite, carnauba wax, lanoline and spermaceti; fatty acids or esters thereof such as stearic acid, palmitic acid, oleic acid, glycerinemonostearate, glycerinedistearate, glycerine monooleate, isopropyl myristate, isopropyl stearate and butyl stearate; higher alcohols such as cetyl alcohol, stearyl alcohol, palmityl alcohol and hexyl dodecyl alcohol; adsorbents or thickening agents such as cationic cellulose, carboxybetaine type polymer and cationic silicone; polyhydric alcohols having a moisture retention action, such as glycol and sorbitol; emulsifying agents for silicone oil, such as polyether-modified silicone, polyether alkyl-modified silicone and glyceryl ether-modified silicone; thickening agents such as methyl cellulose, ethyl cellulose, carboxymethyl cellulose, polyacrylic acid, tragacanth, agar and gelatin; antiperspirants such as aluminum hydroxychloride, aluminum chloride, aluminum sulfate, basic aluminum bromide, aluminum phenol sulfonate and basic aluminum iodide; sterilizers such as 3,4,4-trichlorocarbanilide (TCC), benzalkonium chloride, benzethonium chloride, alkyl trimethyl ammonium chloride, resorcin, phenol, sorbic acid, salicylic acid and hexachlorophene; masking agents such as musk, skatole, lemon oil, lavender oil, absolute, jasmine, vanillin, benzoin, benzyl acetate and menthol and other efficacious components such as emulsion stabilizers, chelating agents, UV protecting agents, pH adjusting agents, preservatives, coloring matters, whitening agents, analgesic antiinflammatory agents, anti-itching agents, disinfectants, astringents, skin softening agents and hormones; water; surfactants; W/O or O/W type emulsifying agents, perfumes, etc.

EXAMPLES

The present invention is described in more detail by reference to the Examples that follow. The Examples are set forth for more illustration of the present invention, and not intended to limit the present invention.

In the Examples, "%" and "parts" refer to "% by weight" and "parts by weight", respectively. The melting point of polyolefin-based resin is a value determined according to JIS K0064:1992.

Example 1

Production of Particles A

Polyolefin-based resin Mitsui Highwax HW-220MP (polyethylene, molecular weight 2000, melting point 107° C., crystallization degree 65%, manufactured by Mitsui Chemicals, Inc.) and zinc oxide FINEX-50S-LP2 (polysiloxane-treated zinc oxide, average primary particle diameter 0.02 μm, manufactured by Sakai Chemical Industry Co., Ltd.) were mixed in a weight ratio of 70:30 (HW-220MP:FINEX-50S-LP2) and kneaded at a screw revolution rate of 200 rpm, at a cylinder temperature of 100° C., at a feed rate of 10 kg/hr with an extruder PCM30 (manufactured by IKEGAI Corporation). Then, a melt admixture of the polyolefin and zinc oxide was spray-cooled into a gaseous phase at 25° C. and recovered as composite particles. The average particle diameter of the particles obtained by cutting coarse particles out through a sifter was 3.3 μm, and the content of zinc oxide in the composite particles, as determined from ignition residues, was 29 wt %.

<Conditions of the Granulator>
Nozzle: 4-fluid straight type nozzle (manufactured by Fujisaki Electric Co., Ltd.)
Admixture temperature: 150° C.
Rate of delivery of admixture: 5 mL/min
Assist air temperature: 500° C.
Assist air flow rate: 50 L/min Example 2

Production of Particles B

The same procedure as in Example 1 was carried out except that polyolefin-based resin Mitsui Highwax HW-220MP (polyethylene, molecular weight 2000, melting point 107° C., crystallization degree 65%, manufactured by Mitsui Chemicals, Inc.), polyolefin-based resin Mitsui Highwax HW-100P (polyethylene, molecular weight 900, melting point 116° C., crystallization degree 90%, manufactured by Mitsui Chemicals, Inc.) and zinc oxide FINEX-50S-LP2 (polysiloxane-treated zinc oxide, average primary particle diameter 0.02 µm, manufactured by Sakai Chemical Industry Co., Ltd.) were mixed in a weight ratio of 35:35:30 (HW-220MP:HW-100P:FINEX-50S-LP2), and the resulting composite particles were recovered. The degree of crystallization of the resin component was 77.5%, the average particle diameter of the particles obtained by cutting coarse particles out through a sifter was 3.7 µm, and the content of zinc oxide in the composite particles, as determined from ignition residues, was 29 wt %.

Comparative Example 1

Production of Particles C

The same procedure as in Example 1 was carried out except that Mitsui Highwax HW-100P (polyethylene, molecular weight 900, melting point 116° C., crystallization degree 90%, manufactured by Mitsui Chemicals, Inc.) was used as the polyolefin-based resin, and the resulting composite particles were recovered. The average particle diameter of the particles obtained by cutting coarse particles out through a sifter was 2.8 µm, and the content of zinc oxide in the composite particles, as determined from ignition residues, was 30 wt %.

Comparative Example 2

Production of Particles D

The same procedure as in Example 1 was carried out except that C105 (polyethylene, molecular weight 1300, melting point 100° C. or more, crystallization degree 88%, manufactured by Shumann Sasol AG) was used as the polyolefin-based resin, and the resulting composite particles were recovered. The average particle diameter of the particles obtained by cutting coarse particles out through a sifter was 3.4 µm, and the content of zinc oxide in the composite particles, as determined from ignition residues, was 29 wt %.

Comparative Example 3

Production of Particles E

FINEX-K2-LP2 (zinc oxide content 75%, manufactured by Sakai Chemical Industry Co., Ltd.), that is, inactivated superfine zinc oxide particles whose surfaces were capsulated with a high-density silica layer were used as the particles in this comparative example.

Comparative Example 4

Production of Particles F

Methyl methacrylate/ethylene glycol dimethacrylate copolymer particles (average particle diameter 10.9 µm, zinc oxide content 14 wt %) containing fine particles of zinc oxide were prepared according to the following method.

(1) Production of a Dispersion of Fine Particles of Oxide Zinc

The following materials were mixed and dispersed for 10 hours with a ball mill to give a dispersion of fine particles of zinc oxide.

| | |
|---|---|
| Fine particles of zinc oxide | 25 parts |
| (FINEX-75, average particle diameter 0.02 µm, manufactured by Sakai Chemical Industry Co., Ltd. Co., Ltd.) | |
| Methyl methacrylate (resin monomer) | 69 parts |
| Sodium dialkyl sulfosuccinate | 6 parts |
| (surfactant Pelex OT-P, manufactured by Kao Corporation) | |

(2) Production of Resin Particles

A resin monomer phase and an aqueous phase, shown below, were mixed with each other and stirred at 800 rpm for 5 minutes in a homomixer such that the diameter of monomer droplets became about 5 µm. Then, the resulting dispersion was transferred to a reaction apparatus equipped with a stirrer and a thermometer, and heated to 55° C. to initiate polymerization. At this temperature, the mixture was polymerized for 5 hours and then cooled to room temperature, and the resulting resin particles were separated by filtration under suction. The particles were washed with a suitable amount of warm water, then washed with methanol and dried at 55° C. for 10 hours to prepare resin particles.

<Resin Monomer Phase>

| <Resin monomer phase> | |
|---|---|
| Dispersion of fine particles of zinc oxide in (1) | 48 parts |
| Methyl methacrylate (resin monomer) | 52 parts |
| Ethylene glycol dimethacrylate | 20 parts |
| (crosslinking agent NK ESTER 1G, manufactured by Shin-nakamura Chemical Co., Ltd.) | |
| 2,2-Azobis-2,4-dimethyl valeronitrile (polymerization initiator) | 0.2 part |
| <Aqueous phase> | |
| Deionized water | 500 parts |
| Polyvinyl alcohol | 10 parts |
| (EG-30, saponification degree 87%, manufactured by Nippon Gosei Co., Ltd.) | |

Test Example 1

Acid Washing Test (Degree of Remaining Zinc Oxide in the Particles After the Treatment with Hydrochloric Acid)

25 mL of 1.0 mol/L aqueous hydrochloric acid solution and 25 mL ethanol were mixed with each other, and the particles in an amount of 1 g in terms of zinc oxide, obtained in each of the Examples and Comparative Examples, were mixed therewith and introduced into a 100-mL screw tube, then set in a shaker (stroke length 10 cm, 100 reciprocations/min.) and shaken at room temperature (25° C.) for 2 hours. The dispersion was filtered under reduced pressure through a PTFE membrane filter having a pore diameter of 0.5 µm, washed with ethanol and dried for 12 hours with hot air at 70° C. by a dryer to give particles after the treatment with hydrochloric acid. Ignition residues obtained by treating the particles at 800° C. for 2 hours were regarded as the amount of zinc oxide in the particles after the treatment with hydrochloric acid, and the degree of remaining zinc oxide in the particles after the treatment with hydrochloric acid was calculated according to the following equation (I). The results are shown in Table 1.

Degree (%) of remaining zinc oxide in the particles after the treatment with hydrochloric acid=(A2/A1)×100  (I)

wherein:
A1: the content (%) of zinc oxide in the particle before the treatment with hydrochloric acid, and
A2: the content (%) of zinc oxide in the particle after the treatment with hydrochloric acid.

Test Example 2

Formulation Stability Test (Stability in UV Care Preparation)

79.12 g purified water, 0.3 g acrylic acid-based thickener (ETD2020, manufactured by BF Goodrich), 0.2 g acrylic acid-based thickener (pemulen TR-2, manufactured by Nikko Chemicals) and 0.2 g methyl paraben were introduced and mixed under stirring so as to be uniform as a whole, and then 0.18 g aqueous triethanol amine solution (effective content 89%) was added thereto and mixed under stirring so as to be uniform as a whole to prepare base gel for evaluation.

The particles for evaluation containing 0.3 g zinc oxide was mixed with 3.0 g ethanol in a 100-ml cup and dispersed uniformly with a ultrasonic dispersing machine. 16.0 g of the base gel for evaluation was mixed therewith and stirred with a high-speed impeller dispersing machine until the mixture became uniform as a whole, and then stored for 3 hours in a room-temperature (25° C.) environment to give gel for evaluation.

The viscosity of the resulting gel for evaluation was measured by a Brookfield viscometer under measurement conditions of 25° C. and 6 rpm, and its outward appearance was observed. The evaluation gel blended with the composite particles in each of the Examples had high viscosity and the particles were uniformly dispersed, while the evaluation gel blended with the evaluation gel in each of the Comparative Examples had viscosity reduced to less than 1000 mPa·s, that is, the lower limit of measurement, and the particles were separated from the liquid when observed with naked eyes.

The evaluation gel blended with the particles in each of the Examples was further stored for 21 days in an environment at 50° C. The viscosity was maintained after storage, and liquid separation was not observed in appearance. A change in viscosity determined according to the following equation (II) is shown in Table 1.

Change in viscosity (%)=($\eta 2/\eta 1$)×100  (II)

wherein:
$\eta 1$: the viscosity (mPa·s) of the evaluation gel when prepared, and
$\eta 2$: the viscosity (mPa·s) of the evaluation gel after storage.

Test Example 3

Optical Property Test (Evaluation of UV-Screening Properties and Transparency)

The particles in an amount of 1 part in terms of zinc oxide, obtained in each of the Examples and Comparative Examples, were mixed with 100 parts of SI-UGE (alkyl glyceryl ether-modified silicone, manufactured by Kao Corporation) and dispersed uniformly with a spatula. The resulting dispersion was placed in a quartz cell having a light path of 50 μm in length, and a difference between transmittance at a wavelength of 550 nm and transmittance at a wavelength of 350 nm measured by a spectrophotometer (UV-2550 manufactured by Shimadzu Corporation) was calculated as ΔT. The results are shown in Table 1. Any composite particles had excellent UV-screening properties and transparency, thus indicating that they had excellent performance as cosmetics.

TABLE 1

| | Test example 1 | Test example 2 | | | Test example 3 |
|---|---|---|---|---|---|
| | Degree of remaining zinc oxide in particles after treatment with hydrochloric acid | Viscosity of evaluation gel when prepared ($\eta 1$)(after 3 hours at 25° C.) | Viscosity after 21 days at 50° C.($\eta 2$) | Change in viscosity | ΔT |
| Particles in example 1 | 99% | 18000 mPa·s | 16000 mPa·s | 83% | 51% |
| Particles in example 2 | 96% | 18000 mPa·s | 16000 mPa·s | 83% | 54% |
| Particles in comparative example 1 | 65% | not more than 1000 mPa·s (separation occurred) | — | — | 50% |
| Particles in comparative example 2 | 56% | not more than 1000 mPa·s (separation occurred) | — | — | 43% |
| Particles in comparative example 3 | — | not more than 1000 mPa·s (separation occurred) | — | — | 67% |
| Particles in comparative example 4 | not more than 3.5% | not more than 1000 mPa·s (separation occurred) | — | — | — |

Example 3

Production of Particles G

Thermoplastic resin Mitsui Highwax HW-220MP (polyethylene, molecular weight 2000, melting point 107° C., crystallization degree 65%, manufactured by Mitsui Chemicals, Inc.) and zinc oxide FINEX-50S-LP2 (polysiloxane-treated zinc oxide, average primary particle diameter 0.02 μm, manufactured by Sakai Chemical Industry Co., Ltd.) were mixed in a weight ratio of 70/30 (polyethylene/zinc oxide) and kneaded at a screw revolution rate of 200 rpm, at a cylinder temperature of 100° C., at a feed rate of 10 kg/hr with an extruder PCM30 (manufactured by IKEGAI Corporation). Then, the resulting admixture, at a spray nitrogen/admixture ratio of 21000/1 by volume at 150° C., was spray-cooled into a gaseous phase at 25° C. through a straight type 4-fluid nozzle (Micro Mist Dryer MDL-050C, manufactured by Fujisaki Electric Co., Ltd.), and recovered as composite particles. The average particle diameter of the resulting particles was 12.4 μm, and the content of particles having a particle diameter of 5 μm or less was 15.8 vol %.

Example 4

Production of Particles H

The same procedure as in Example 3 was carried out except that a pencil type 3-fluid nozzle (Micro Mist Dryer MDL-050C, manufactured by Fujisaki Electric Co., Ltd.) was used as the spray nozzle, and the resulting composite particles were recovered. The volume-average particle diameter of the resulting particles was 8.4 μm, and the content of particles having a particle diameter of 5 μm or less was 27.1 vol %.

Example 5

Production of Particles I

The same procedure was carried out as in Example 4 except that thermoplastic resin Mitsui Highwax HW-220MP (polyethylene, molecular weight 2000, melting point 107° C., crystallization degree 65%, manufactured by Mitsui Chemicals, Inc.), thermoplastic resin Mitsui Highwax HW-100P (polyethylene, molecular weight 900, melting point 116° C., crystallization degree 90%, manufactured by Mitsui Chemicals, Inc.) and zinc oxide FINEX-50S-LP2 (polysiloxane-treated zinc oxide, average primary particle diameter 0.02 μm, manufactured by Sakai Chemical Industry Co., Ltd.) were used and mixed in an HW-220MP/HW-100P/zinc oxide ratio of 35/35/30 by weight, and the resulting composite particles were recovered. The volume-average particle diameter of the resulting particles was 5.4 μm, and the content of particles having a particle diameter of 5 μm or less was 52.1 vol %.

Example 6

Production of Particles J

The same procedure was carried out as in Example 5 except that the spray nitrogen/admixture ratio by volume was 10000/1, and the resulting composite particles were recovered. The volume-average particle diameter of the resulting particles was 5.8 μm, and the content of particles having a particle diameter of 5 μm or less was 50.2 vol %.

The spraying conditions and results in Examples 3 to 6 are collectively shown in Table 2.

TABLE 2

| | Example 3 | Example 4 | Example 5 | Example 6 |
|---|---|---|---|---|
| Spray nozzle | 4-fluid nozzle Straight type | 3-fluid nozzle Pencil type | 3-fluid nozzle Pencil type | 3-fluid nozzle Pencil type |
| Spraying conditions | | | | |
| Spray nitrogen/admixture (volume ratio) | 21000/1 | 21000/1 | 21000/1 | 10000/1 |
| Spray temperature (° C.) | 150 | 150 | 150 | 150 |
| Viscosity on spraying (mPa · s) | 80 | 80 | 50 | 50 |
| Composite particles | | | | |
| Volume-average particle diameter(μm) | 12.4 | 8.4 | 5.4 | 5.8 |
| Content of particles having a particle diameter of 5 μm or less (vol %) | 15.8 | 27.1 | 52.1 | 50.2 |

Example 7

Production of Particles K

Polyethylene (trade name: HW-100P, molecular weight 900, manufactured by Mitsui Chemicals, Inc.) and zinc oxide (trade name: Finex 50S-LP2, polysiloxane-treated zinc oxide, average primary particle diameter 0.02 μm, manufactured by Sakai Chemical Industry Co., Ltd.) were mixed in a weight ratio of 70:30 and kneaded at a screw revolution rate of 200 rpm, at a cylinder temperature of 30° C. to 60° C. to 100° C. to 100° C. to 100° C. to 100° C. to 100° C., at a feed rate of 10 kg/hr with an extruder PCM30 (manufactured by IKEGAI Corporation). Then, the resulting admixture was formed into particles with a spray cooling granulator under the following conditions to give particles K having an average particle diameter of 3.8 μm. The content of zinc oxide in the particles, as determined from ignition residues, was 29 wt %.

<Conditions of the Granulator>
Nozzle: 4-fluid straight type nozzle (manufactured by Fujisaki Electric Co., Ltd.)
Admixture temperature: 150° C.
Rate of delivery of admixture: 5 mL/min
Assist air temperature: 500° C.
Assist air flow rate: 50 L/min

Example 8

Production of Particles L

The same procedure as in Example 7 was carried out except that C105 (molecular weight 1300, manufactured by Shumann Sasol AG) was used as the polyethylene, and particles L having an average particle diameter of 3.4 μm were recovered. The content of zinc oxide in the particles, as determined from ignition residues, was 29 wt %.

Example 9

Production of Particles M 3.0 g particles K were mixed with 200 mL of 0.1% aqueous solution of potassium monomyristyl phosphate (MAP-40H manufactured by Kao Corporation), and then dispersed for 3 minutes at 5000 rpm with a homomixer. The dispersion was filtered under reduced pressure with a PTFE membrane filter having a pore size of 0.45 μm, and then washed by filtration with 100 mL deionized water, 50 mL ethanol and 50 mL ethanol in this order, to give ethanol slurry of the particles K treated with the anionic surfactant.

Example 10

Production of Particles N

The same procedure as in Example 9 was carried out except that particles L were used in place of particles K, and 0.1% cocoyl methyl taurine (trade name: Nikkol CMT-30, manufactured by Nikko Chemicals) was used as the anionic surfactant, to give ethanol slurry of the particles L treated with the anionic surfactant.

Test Example 4

The particles in Examples 9 and 7 were evaluated for formulation stability. The results are shown in Table 3.

<Method of Evaluating Formulation Stability>
79.12 g purified water, 0.3 g acrylic acid-based thickener (ETD2020, manufactured by BF Goodrich), 0.2 g acrylic acid-based thickener (pemulen TR-2, manufactured by Nikko Chemicals) and 0.2 g methyl paraben were introduced and mixed under stirring so as to be uniform as a whole, and then 0.18 g aqueous triethanol amine solution (effective content 89%) was added thereto and mixed under stirring so as to be uniform as a whole to prepare base gel for evaluation.

The particles for evaluation containing 0.2 g zinc oxide, and 1.7 g ethanol, were introduced into a 20-mL glass tube container and dispersed uniformly with an ultrasonic dispersing machine. 3.0 g of the base gel for evaluation was added thereto and stirred with a pencil mixer until the mixture became uniform as a whole, to give gel for evaluation. This gel for evaluation was stored in an environment at 50° C., and the time required for the gel to be separated into two layers was measured.

TABLE 3

| | Content of zinc oxide in particles (%) | Time required for separation to occur |
|---|---|---|
| Example 9 | 29 | 30 hours or more |
| Example 7 | 29 | Less than 3 hours |

Test Example 5

The particles in Examples 10 and 8 were evaluated for formulation stability in the following method. The results are shown in Table 4.

<Method of Evaluating Formulation Stability>
An O/W type UV care gel was prepared in a procedure shown below. The resulting gels were placed in a 100-mL screw tube, stored for 7 days and 14 days respectively in a thermostatic environment at 50° C., and measured for a change in viscosity during the storage.

Procedure of Preparing the O/W Type UV Care Gel
1) 95% synthetic ethanol (32.5 g) was mixed with 2-ethylhexyl p-methoxycinnamate (8.5 g). The resulting solution is referred to solution a.
2) Purified water (39.5 g) was mixed with disodium edetate (0.01 g), and Carbopole ETD2020 (acrylic acid-based thickener, 0.3 g) was uniformly mixed therewith under stirring with a high-speed impeller dispersing machine. The resulting solution is referred to as solution b.
3) 95% synthetic ethanol (9.0 g) and the particles for evaluation (7.0 g) were mixed uniformly with each other with a high-speed impeller dispersing machine. The resulting solution is referred to solution c.
4) Under stirring with a propeller, the solutions a and b were mixed with Aculine 22 (thickening emulsifier, 0.60 g), and then the solution c was gradually mixed therewith. The mixture was sufficiently stirred. The resulting solution is referred to as solution d.
5) The solution d was dispersed with a dispersing machine such as a homomixer, to prepare an O/W dispersion observed to be uniform.
6) A mixture of 2-amino-2-methyl-1-propanol (0.08 g) and purified water (0.5 g) was mixed with the solution d under stirring with a propeller, and then concentrated glycerin (0.5 g) was mixed therewith.

Composition of the O/W Type UV Care Gel

| | |
|---|---|
| 95% synthetic alcohol | 41.50% |
| 2-Ethylhexyl p-methoxycinnamate | 8.50 |
| Evaluation particles | 7.00 |
| Carbopole ETD2020 (BF Goodrich) | 0.30 |
| Aculine 22 (ROHM AND HASS Company) | 0.60 |
| Concentrated glycerin for cosmetics | 0.50 |
| 2-Amino-2-methyl-1-propanol | 0.08 |
| Disodium edetate | 0.01 |
| Purified water | balance |

Measurement of Viscosity
A screw tube containing the O/W type UV care gel was shaken well with hands before measurement, and then dipped for 30 minutes in a water bath set at 25° C., and then the viscosity was measured by a Brookfield viscometer. The measurement conditions were 30 rpm, rotor No. 4, and 1 minute. The sample was measured for viscosity after storage at 50° C. for 7 days and 14 days respectively, and a change in viscosity, relative to the viscosity (100%) of the sample just after blended, was calculated according to the following equation.

Change in viscosity (%)=(η2/η1)×100 wherein:
η1: the viscosity (mPa·s) of the UV care gel just after blended, and
η2: the viscosity (mPa·s) of the UV care gel after storage.

TABLE 4

| | Content of zinc oxide in particles | Change in viscosity (%) | |
|---|---|---|---|
| | (%) | 7 days | 14 days |
| Example 10 | 29 | 97 | 77 |
| Example 8 | 29 | 79 | 45 |

Example 11

Production of Particles O

Polyethylene (trade name: C105, molecular weight 1300, manufactured by Shumann Sasol AG) and zinc oxide (trade name: FINEX-50S-LP2, polysiloxane-treated zinc oxide, average primary particle diameter 0.02 μm, manufactured by Sakai Chemical Industry Co., Ltd.) were mixed in a weight ratio of 70:30 and kneaded at a screw revolution rate of 200 rpm, at a cylinder temperature of 30° C. to 60° C. to 100C to 100° C. to 100° C. to 100° C. to 100° C., at a feed rate of 10 kg/hr with an extruder PCM30 (manufactured by IKEGAI Corporation). The resulting admixture was formed into particles with a spray cooling granulator under the following conditions to give particles O having an average particle diameter of 3.4 μm. The content of zinc oxide in the particles, as determined from ignition residues, was 30 wt %.

<Conditions of the Granulator>
Nozzle: 4-fluid straight type nozzle (manufactured by Fujisaki Electric Co., Ltd.)
Admixture temperature: 150° C.
Rate of delivery of admixture: 5 mL/min
Assist air temperature: 500° C.
Assist air flow rate: 50 L/min Examples 12

Production of Particles P

The particles O were used in this example. 250 mL of 0.5 mol/L phosphoric acid solution (solvent composition: water/ethanol=50/50 (ratio by volume)) was prepared, then mixed with 15 g particles O, introduced into a polyethylene container and shaken for 4 hours with a shaker (stroke length 10 cm, 100 reciprocations/min.).

After shaking, the resulting dispersion of the particles o and 1000 mL deionized water were introduced into a separatory funnel and shaken well. The particles floated on the surface of the liquid, and the lower-layer solution not containing the particles O was discarded, and 1000 mL deionized water was added to the particles, and the lower-layer solution only was discarded again. This operation was repeatedly carried out until the lower-layer solution showed pH 6 to 8 with a pH testing paper (pH testing paper UNIV, manufactured by Advantec Toyo Co., Ltd.). The resulting aqueous dispersion of the particles O was filtered through a 3.0 μm membrane filter and dried sufficiently in an environment at 60° C. under reduced pressure to give the particles O treated with phosphoric acid. The content of zinc oxide in the composite particles after the treatment, as determined from ignition residues, was 17 wt %.

Example 13

Production of Particles Q

Particles O treated with succinic acid were obtained by the same acid treatment as in Example 12 except that the particles O were used, and 0.5 mol/L succinic acid solution (solvent composition: water/ethanol=50/50 (ratio by volume)) was used in place of phosphoric acid. The content of zinc oxide in the composite particles after the treatment, as determined from ignition residues, was 16 wt %.

The particles in Examples 11, 12 and 13 were examined in a formulation stability test by the following method. The results are shown in Table 5.

<Method of Evaluation Formulation Stability>
An O/W type UV care gel was prepared in a procedure shown below. The resulting gel was placed in a 100-mL screw tube, stored for 3 weeks in a thermostatic environment at 50° C., and measured for a change in viscosity during the storage.

Procedure of Preparing the O/W Type UV Care Gel 1) 95% synthetic ethanol (32.5 g) was mixed with 2-ethylhexyl p-methoxycinnamate (8.5 g). The resulting solution is referred to solution a.
2) Purified water (39.5g) was mixed with disodium edetate (0.01 g), and Carbopole ETD2020 (acrylic acid-based thickener, 0.3 g) was uniformly mixed therewith under stirring with a high-speed impeller dispersing machine. The resulting solution is referred to as solution b.
3) 95% synthetic ethanol (9.0 g) and the particles for evaluation (7.0 g) were mixed uniformly with each other with a high-speed impeller dispersing machine. The resulting solution is referred to solution c.
4) Under stirring with a propeller, the solutions a and b were mixed with Aculine 22 (thickening emulsifier, 0.60 g), and then the solution c was gradually mixed therewith. The mixture was sufficiently stirred. The resulting solution is referred to as solution d.
5) The solution d was dispersed with a dispersing machine such as a homomixer, to prepare an O/W dispersion observed to be uniform.
6) A mixture of 2-amino-2-methyl-1-propanol (0.08 g) and purified water (0.5 g) was mixed with the solution d under stirring with a propeller, and then concentrated glycerin (0.5 g) was mixed therewith.

Composition of the O/W Type UV Care Gel

| | |
|---|---|
| 95% synthetic alcohol | 41.50% |
| 2-Ethylhexyl p-methoxycinnamate | 8.50 |
| Evaluation particles | 7.00 |
| Carbopole ETD2020 (BF Goodrich) | 0.30 |
| Aculine 22 (ROHM AND HASS Company) | 0.60 |
| Concentrated glycerin for cosmetics | 0.50 |
| 2-Amino-2-methyl-1-propanol | 0.08 |
| Disodium edetate | 0.01 |
| Purified water | balance |

Measurement of Viscosity

A screw tube containing the O/W type UV care gel was shaken well with hands before measurement, and then dipped for 30 minutes in a water bath set at 25° C., and then the viscosity was measured by a Brookfield viscometer. The measurement conditions were 30 rpm, rotor No. 4, and 1 minute. The viscosity after storage at 50° C. for 3 weeks, as compared with the viscosity (100%) just after blended, was determined as change in viscosity, according to the following equation.

$$\text{Change in viscosity (\%)} = (\eta 2/\eta 1) \times 100$$

wherein:
$\eta 1$: the viscosity (mPa·s) of the UV care gel just after blended, and
$\eta 2$: the viscosity (mPa·s) of the UV care gel after storage.

TABLE 5

| | Content of zinc oxide in particles (%) | Change in viscosity (%) |
|---|---|---|
| Example 12 | 17 | 81 |
| Example 13 | 16 | 82 |
| Example 11 | 30 | 22 |

The invention claimed is:

1. A process for producing composite particles comprising:
   mixing a polyolefin-based resin having a crystallization degree of 80% or less with zinc oxide, thereby forming a mixture;
   heating the mixture to a temperature not lower than a softening point or melting point of the polyolefin-based resin, thereby producing a thermally melt admixture; and
   cooling and solidifying the admixture by spraying the admixture into a refrigerant,
   wherein the polyolefin-based resin is acid-modified polyethylene.

2. The process for producing composite particles according to claim 1, wherein the composite particles, after having been dipped for 2 hours at 25° C. in a mixture of 0.5 mol/L aqueous hydrochloric solution and an equal volume of ethanol, retain 50 wt % or more of the zinc oxide present in said composite particles before having been dipped.

3. The process for producing composite particles according to claim 1, wherein a weight ratio of polyolefin-based resin to zinc oxide in the composite particles is from 99/1 to 30/70.

4. The process for producing composite particles according to claim 1, wherein the particles have a volume-average particle diameter of 0.5 to 30 μm.

5. The process for producing composite particles according to claim 1, wherein spraying the mixture comprises spraying with a 3-fluid or more nozzle.

6. The process for producing composite particles according to claim 5, wherein the 3-fluid or more nozzle is a straight nozzle or a pencil nozzle.

7. The process for producing composite particles according to claim 1, wherein the admixture is sprayed together with a compressed gas into the refrigerant and the compressed gas/admixture ratio by volume is 1000/1 to 100,000/1.

8. The process for producing composite particles according to claim 5, wherein the polyolefin-based resin has a crystallization degree of 70% or less.

9. The process for producing composite particles according to claim 1, wherein the softening point or melting point of the polyolefin-based resin is 80° C. or more.

10. The process for producing composite particles according to claim 1, wherein the softening point or melting point of the polyolefin-based resin is 100° C. or more.

11. The process for producing composite particles according to claim 1, wherein the softening point or melting point of the polyolefin-based resin is 200° C. or less.

12. The process for producing composite particles according to claim 1, wherein the polyolefin-based resin has a molecular weight of from 500 to 20000.

13. The process for producing composite particles according to claim 1, wherein the polyolefin-based resin has a molecular weight of from 1000 to 10000.

14. The process for producing composite particles according to claim 1, wherein the proportion of particles having a maximum particle diameter of 5 μm is 15 volume % or more.

15. The process for producing composite particles according to claim 1, wherein the zinc oxide has a maximum particle diameter of 0.1 μm.

16. The process for producing composite particles according to claim 1, wherein a weight ratio of polyolefin-based resin to zinc oxide in the composite particles is from 95/5 to 50/50.

17. The process for producing composite particles according to claim 1, wherein a weight ratio of polyolefin-based resin to zinc oxide in the composite particles is from 80/20 to 60/40.

18. The process for producing composite particles according to claim 1, wherein the particles have a volume-average particle diameter of 2 to 10 μm.

* * * * *